United States Patent [19]
Fritsch et al.

[11] Patent Number: 4,725,537
[45] Date of Patent: Feb. 16, 1988

[54] ASSAY, REAGENT AND KIT EMPLOYING NUCLEIC ACID STRAND DISPLACEMENT AND RESTRICTION ENDONUCLEASE CLEAVAGE

[75] Inventors: Edward F. Fritsch, Concord, Mass.; Jon I. Williams, Montclair, N.J.

[73] Assignees: Allied Corporation, Morris Township, Morris County, N.J.; Genetics Institute, Inc., Cambridge, Mass.

[21] Appl. No.: 777,657

[22] Filed: Sep. 19, 1985

[51] Int. Cl.⁴ .................. G01N 33/53; G01N 33/566; C12Q 1/68
[52] U.S. Cl. .......................................... 435/6; 435/7; 435/810; 436/501; 536/27; 536/28; 935/77; 935/78
[58] Field of Search ............... 435/6, 7, 810; 436/501; 935/77, 78; 536/27, 28

[56] References Cited
FOREIGN PATENT DOCUMENTS
0142299 5/1985 European Pat. Off. ................ 435/6

Primary Examiner—Robert J. Warden
Assistant Examiner—Jack Spiegel
Attorney, Agent, or Firm—Alan M. Doernberg

[57] ABSTRACT

A target nucleotide sequence having a half-restriction site is determined in the nucleic acid of a biological sample. It is contacted with a reagent complex of:
(i) a labeled probe polynucleotide containing a target binding region which is substantially complementary to the target nucleotide sequence and which contains a unique half-restriction site completely complementary to the half-restriction site of the target nucleotide sequence; and
(ii) a second polynucleotide hybridized to the labeled probe polynucleotide in at least a portion of the target binding region, the portion including the unique half-restriction site of the target binding region;

The second polynucleotide contains at least one mismatched or unpaired nucleotide opposite to the unique half-restriction site of the labeled probe polynucleotide, whereby a restriction enzyme specific for the unique restriction site will not cleave the reagent complex. The target nucleotide sequence, if present, displaces the second polynucleotide from the target nucleotide region and forms the unique restriction site in double-stranded form. The labeled probe polynucleotide is then cleaved at the unique restriction site in double-stranded form to form labeled cleavage fragment, which is detected.

25 Claims, 1 Drawing Figure

ASSAY, REAGENT AND KIT EMPLOYING NUCLEIC ACID STRAND DISPLACEMENT AND RESTRICTION ENDONUCLEASE CLEAVAGE

BACKGROUND OF THE INVENTION

The present invention relates to methods, reagents and kits for the determination (qualitatively or quantitatively) of the presence of target nucleotide sequences, and particularly for determining the presence of target nucleotide sequences such as the structural genes for globin proteins or blood factor proteins where such sequences in double-stranded nucleic acid strands contain one or more restriction endonuclease cleavage sites.

Nucleic acid detection assays of various types have been documented in the technical and patent literature. These types of assays, and particularly those requiring detection of polynucleotides, in large part are based on the purine-pyrimidine base pairing properties of complementary nucleic acid strands in DNA-DNA or DNA-RNA duplices where DNA refers to deoxyribonucleic acid and RNA refers to ribonucleic acid. This base pairing process most frequently occurs through formation of hydrogen bonds in the pairing of adenosine-thymine (A-T) and guanosine-cytosine (G-C) bases in double-stranded DNA; adenosine-uracil base pairs may additionally be formed by hydrogen bonding in DNA-RNA hybrid molecules, as may A-T and G-C pairs. Base pairing of nucleic acid strands for determination of the presence or absence of a given nucleotide sequence typically occurs between sample nucleotide sequences and a probe polynucleotide (referred to hereinafter also as a probe nucleotide sequence) and is commonly termed nucleic acid hybridization or simply hybridization.

Frequently (as in U.S. Pat. No. 358,535 issued to Falkow et al. (1982)), nucleic acid hybridization assays require the sample nucleotide sequences to be immobilized to or on a solid matrix or substrate and to be rendered single-stranded if not already present in that form. The immobilized sample nucleotide sequences are then washed extensively before exposure to labeled probe polynucleotides. A specific application of nucleic acid hybridization technology of this type is described in U.S. Pat. No. 4,395,486 issued to Wilson et al. (1983) which proposes an assay limited to the detection of the rare structural gene for hemoglobin S. The assay described therein first obtains double-stranded sample or analyte DNA in a native double-stranded form and then subjects the contents of the reaction mixture to enzymatic cleavage by the restriction endonuclease Dde I. Restriction fragments including unique fragments of 175 and 201 nucleotide base pairs in length arise from a gene for hemoglobin A or including a unique fragment of 376 nucleotide base pairs in length arise from a gene for hemoglobin S. Thus the genotypes for normal (AA) individuals and for homozygous individuals with sickle cell disease (SS) can each be detected by physical analysis of the restriction endonuclease cleavage products by such methods as gel electrophoresis of the restricted DNA and subsequent detection of nucleotide sequences containing the appropriate portions of a hemoglobin gene by the blotting method of E. M. Southern (*Journal of Molecular Biology* vol. 98, pp. 503–517 (1975)). The presence of all three fragments in Southern blots is indicative of the heterozygous sickle cell trait (i.e., the AS genotype).

A group of inventors including some of the present inventors have described a polynucleotide sequence hybridization assay involving polynucleotide strand displacement in the copending application U.S. Ser. No. 607,885, filed May 7, 1984. Such an assay is based upon the selective displacement of a labeled polynucleotide from a complementary probe nucleotide sequence by an appropriate target nucleotide sequence (if present) and subsequent detection of the displaced labeled polynucleotide. Nucleic acid detection assays of this type with hybridization rate modifiers present during the nucleic acid strand displacement step of the assay are described in applications U.S. Ser. No. 684,305 and 684,308, each filed Dec. 20, 1984, and authored by the same aforementioned group of inventors. These assay methods each have limitations in determining the presence of target nucleotide sequences with single purine or pyrimidine base changes as compared to reference target nucleotide sequences.

A group of inventors including some of the present inventors have separately described in application U.S. Ser. No. 652,218, filed Sept. 19, 1984, a nucleic acid diagnostic assay based upon hybridization of analyte DNA to a labeled probe polydeoxynucleotide, cleavage of the product double-stranded DNA hybrid at a restriction site formed upon DNA duplex formation and detection of any cleaved and labeled double-stranded DNA fragments. While this method can detect certain single base changes at specified sites in analyte DNA strands, it has the potential drawback of an appropriate restriction site forming non-specifically at the half-restriction endonuclease recognition site of the labeled probe polydeoxynucleotide, leading to false positive results in the assay. Such a drawback may be reduced or eliminated by selecting conditions whereby productive (i.e., stable) nucleic acid hybridization events occur only when reasonably long tracts of base pairing (e.g., greater than about 10 base pairs) are allowed prior to the next step of the assay; such conditions may, however, impose certain limiting conditions on the procedure used in the assay.

BRIEF DESCRIPTION OF THE INVENTION

The present invention represents an improvement over the method of application U.S. Ser. No. 652,218 in that a second polynucleotide is provided to protect the half-restriction endonuclease recognition site of a labeled probe polynucleotide (hereinafter also referred to as a labeled probe) against non-specific hybridization and/or non-specific nucleolytic cleavage (especially that mediated by a restriction endonuclease). Hybridization of target nucleotide sequences (if present) to the present labeled probed polynucleotide-second (protecting) polynucleotide reagent complex then leads to specific displacement of the protecting polynucleotide from the reagent complex and formation of a target polynucleotide-labeled probe polynucleotide hybrid molecule which is susceptible to cleavage by a restriction endonuclease present in the reaction mixture; whereas the starting reagent complex is not susceptible to such cleavage. In those forms of the present invention wherein the second and protecting polynucleotide is also labeled (such that the present labeled probe polynucleotide-protecting polynucleotide reagent complex is also a form of the reagent complex as defined in application U.S. Ser. No. 607,885), the possibility exists of detecting a second and potentially a qualitatively different signal. Comparison or interaction of the two signals can provide information about the presence and quantity of a class of nucleic acid sequences, or about the presence, quantity and proportion of a particular member of a class of nucleic acid sequences (e.g., the presence of structural genes for hemoglobin and the proportion of such genes which are of genotype A or of genotype S).

Accordingly, the present invention provides a method for determining a target nucleotide sequence having a half-restriction site in the nucleic acid of a biological sample which comprises the steps:

(a) providing a reagent complex of:

(i) a labeled probe polynucleotide containing a target binding region which is substantially complementary to the target nucleotide sequence and which contains a unique half-restriction site completely complementary to the half-restriction site of the target nucleotide sequence; and (ii) a second polynucleotide hybridized to the labeled probe polynucleotide in at least a portion of the target binding region, the portion including the unique half-restriction site of the target binding region;

the second polynucleotide containing at least one (and preferably two or more) mismatched or unpaired nucleotide opposite to the unique half-restriction site of the labeled probe polynucleotide, whereby a restriction enzyme specific for the unique restriction site will not cleave the reagent complex;

(b) contacting the reagent complex with the sample under conditions in which the target nucleotide sequence, if present, will displace the second polynucleotide from the target binding region and form the unique restriction site in double-stranded form;

(c) specifically cleaving the labeled probe polynucleotide at the unique restriction site in double-stranded form to produce a labeled cleavage fragment; and (d) detecting the labeled cleavage fragment.

The present invention further provides a reagent complex comprising the labeled probe polynucleotide (i) and the second polynucleotide (ii) as described above. The present invention also provides a kit comprising a reagent complex as described above and a restriction endonuclease capable of specifically cleaving at the unique half-restriction site when target polynucleotide-probe polynucleotide DNA duplices are produced which include a perfect match at such site.

DETAILED DESCRIPTION OF THE INVENTION

The present invention is an improved form of the invention of co-pending application U.S. Ser. No. 652,218, but also uses a nucleic acid strand displacement event as in co-pending applications U.S. Ser. No. 607,885, 684,305 and 684,308, all of which are incorporated herein by reference. Accordingly, the nomenclature used in those applications, generally as defined therein, is also incorporated by reference in this application and is used in the following description of the current invention.

In the present description, an illustrative embodiment of the invention is shown in FIGS. 1A–1D, is discussed in detail herein and is compared to the embodiments of the earlier applications mentioned above. Thereafter, broader forms and various alternatives useful in the present invention are described.

Figure 1A:
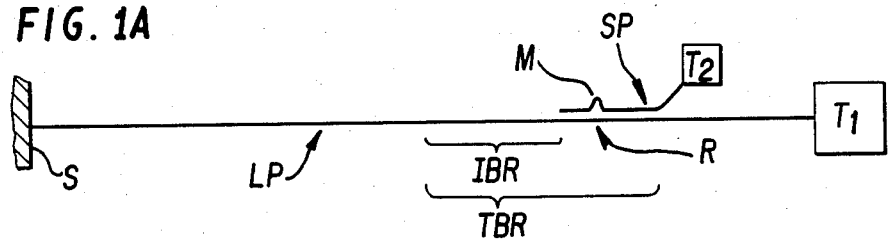

FIG. 1A illustrates an immobilized reagent complex according to one form of the present invention. A labeled probe polynucleotide LP is shown with one of its ends immobilized to or on a solid support and the other one of its ends tagged by attachment of a detectable moiety $T_1$. A number of chemistries can be used either for immobilizing the probe polynucleotide (also known as the probe strand) to or on the solid support or for attaching detectable moieties to the probe strand. Illustrative examples of such chemistries, are discussed in patent application U.S. Ser. No. 729,700, filed May 2, 1985, of E. Brown, et al.

Alternatively, the tag may be attached to an oligonucleotide which is hybridized to the probe strand, as illustrated in the Example below.

The detectable moiety $T_1$ as shown in FIG. 1A can be a radionucleotide, a fluorescent tag, an enzymatic or enzyme cofactor tag, a series of 3' terminal ribonucleotides (as described in co-pending application U.S. Ser. No. 729,503 of Vary et al., filed May 2, 1985) or any of the other various other direct or indirect tags described in any of the abovereferenced patent applications. For illustrative purposes, it can be assumed that the 5' end of the labeled probe polynucleotide LP is immobilized to the support by the attachment chemistry and ligation of Brown et al., application U.S. Ser. No. 729,700, filed May 2, 1985, while the tag $T_1$ is an enzyme attached by similar chemistries and ligation. A portion, termed the target binding region (TBR), contained within the purine and pyrimidine base sequence of the labeled probe polynucleotide LP has been chosen to be complementary to a target nucleotide sequence (TNS of FIGS. 1B and 1C) which is desired to determine if it is present in a sample mixture. Such complementarity may be exact or may provide for a limited number of mismatches except in the region R described more fully below. A second polynucleotide (SP) is bound to a portion of the TBR by hydrogen bonds between purine/pyrimidine base pairs and may or may not contain a distinctly detectable tag $T_2$, depending upon the conditions under which the detectable tags are to be sensed. For illustrative purposes, it can be assumed that tag $T_2$ exists and is a second enzyme of different activity than the activity of enzyme tag $T_1$ (e.g., the enzymes of tags $T_1$ and $T_2$ could be coordinately acting enzymes as part of an enzyme cascade or could catalyze independent reactions, the products of which are each monitored). The base pairing between the second polynucleotide SP and a portion of the TBR in the probe polynucleotide contains at least one base pair mismatch at a locus shown as M on the second polynucleotide SP where M is adjacent to but does not perfectly pair with nucleotides in the region R of the labeled probe LP. As illustrated in FIG. 1A, a further portion of the TBR of the labeled probe polynucleotide LP is in single-stranded form, and is thus referred to as an initial binding region (IBR).

Region R of the target binding region TBR is chosen to be a half-restriction site domain. By the term "half-restriction site" it is meant that when such a region is bound by complementary base pairing to a perfectly matched complementary nucleic acid strand throughout the region R, the double-stranded product region R—R' (see FIG. 1C) will form a site specifically recognizable and cleavable by a restriction endonuclease enzyme. In the method of the present invention, such a product region susceptible to the action of a restriction endonuclease will only form when some portion of the contiguous base sequence on the labeled probe polynucleotide LP (such portion necessarily including the IBR of LP) also binds to a portion of the target nucleotide sequence TNS (such portion in the TNS preferably being immediately adjacent to the product region R-R'). Such restriction endonucleases and their specific restriction endonuclease recognition sequences are well known, being described, for example in *The Enzymes,* Volume 14, P.D. Boyer, ed. (Academic Press, New York, NY; 1981), pp. 138-191. In most cases, such restriction endonuclease recognition sites comprise four or more adjacent nucleotides in a specific and frequently unique sequence within the target binding region TBR. As shown in FIG. 1A, the half-restriction site R is preferably intermediate within the base paired region formed by nucleic acid strand hybridization between the second polynucleotide SP and the labeled probe polynucleotide LP. In order to avoid a non-specific dissociation at this site once the product region R-R' of FIG. 1B has formed, it is preferred that the half-restriction site R be intermediate within the base sequence TBR of the labeled probe polynucleotide LP in the sense that it is no closer than five and preferably no closer than ten nucleotides from either end of the target binding region TBR. Having the half-restriction site be intermediate within TBR may also improve the specificity of the method for a particular target nucleotide sequence TNS.

When the second polynucleotide-labeled probe reagent complex of FIG. 1A is contacted under reaction conditions with the restriction endonuclease specific for the unique product restriction site R-R' (i.e., when the base pairing in this region of the partially or wholly double-stranded product DNA is in its perfectly matched form), then no cleavage is expected to occur. A base pair mismatch due to even a single base in either the second polynucleotide SP or the labeled probe polynucleotide LP within the restriction site region R (comparing locus M of FIG. 1A with the perfectly matched complementary sequence R' for the locus R) should suffice under most conditions to prevent any endonucleolytic restriction events. Nevertheless, it may be preferred to have at least two mismatched nucleotides within segment M opposite the half-restriction site R. Base deletions, insertions or inversions would generally serve as the equivalent of such mismatches.

Figure 1B:
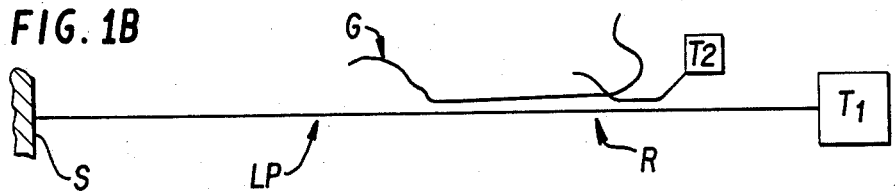

FIG. 1B illustrates the hybridization of a sample polynucleotide G to the labeled probe polynucleotide. As illustrated (and as described more fully in application U.S. Ser. No. 607,885), nucleation will normally occur within the single-stranded initial binding region (IBR) followed by lengthening of the double-stranded region between sample polynucleotide G and labeled probe polynucleotide LP as the polynucleotide strand G migrates into the region of the target binding region (TBR) where the second polynucleotide SP had previously been bound. FIG. 1B illustrates the state of the present method at which such strand migration has reached the region at or near the half-restriction site R. At this point, the second polynucleotide SP (with its potentially existent detectable tag $T_2$) has not yet been fully displaced from the labeled probe polynucleotide LP. Nevertheless, base pairing has occurred at the half-restriction site R between some portion of the sample polynucleotide G and some portion of the labeled probe polynucleotide LP. Provided that the same polynucleotide G has the perfectly specific matched sequence R' that is complementary to the half-restriction site R and is thus a target polynucleotide sequence of interest, a full restriction endonuclease recognition site (R-R') for the restriction endonuclease of the present method has now formed. If a sample strand is otherwise perfectly matched to the TBR, but contains a different nucleotide within region R', then no such site will form, but displacement will still proceed.

Figure 1C:
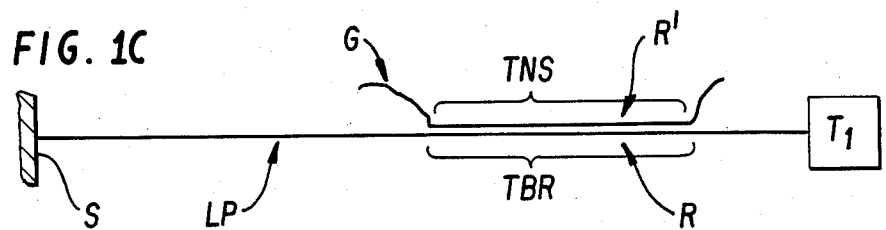

FIG. 1C illustrates the completion of target polynucleotide strand lengthening and migration such that the sample target polynucleotide G is now as fully bound to a target binding region TBR of the labeled probe polynucleotide LP as is stable based upon complementary base pairing and the reaction mixture conditions chosen for the method of the present invention. This state of reaction progression is expected to occur only under favorable thermodynamic or kinetic circumstances, especially including those circumstances where completely or nearly completely perfect base pair complementarity exists between the sample polynucleotide G and some portions of both the IBR and TBR of the labeled probe polynucleotide LP, which portion of TBR includes the half-restriction site R. If these conditions are not met, then it would be expected that reactions would not proceed to a state where either the second polynucleotide SP is completely displaced from the reagent complex or a perfect (restriction site R-R' (a restriction endonuclease recognition site) has formed. In either of these two cases, no label or labels distinguishable from those in the initial reagent complex are likely to be found in a detectable form as required by the assay method of the present invention. Some background signal of label or labels that are rendered detectable during reaction with sample polynucleotides G and that are in a form distinguishable from those in the initial reagent complex may appear during the method of the present invention due to such non-specific events as the presence of indiscriminate endo- or exonucleolytic digestive enzymes, contamination of the reaction mixtures with heavy metal salts yielding cations such as ferrous ion, etc. Such background signal should, however, be small if the physical conditions of reaction for the present method are appropriately chosen.

Figure 1D:
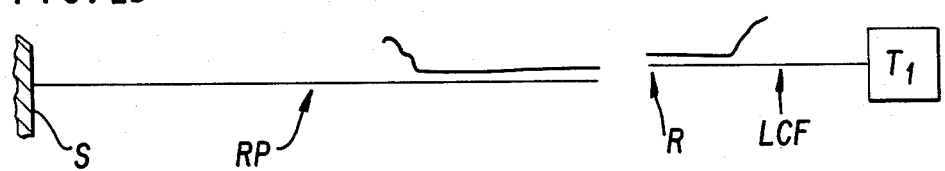

In FIG. 1C, the second polynucleotide SP has been completely displaced in a favorable event mediated by a target nucleotide sequence (TNS) and may be separated and detected at this point in one of the manners described in or incorporated into patent application U.S. Ser. No. 607,885. Assuming, as is shown in FIG. 1C, that the target nucleotide sequence TNS of the sample polynucleotide G is perfectly matched at the half-restriction site R, a restriction endonuclease recognition site will be now formed. By contacting this reaction intermediate with an appropriate restriction endonuclease enzyme, cleavage is now obtained to form the structures shown in FIG. 1D. In FIG. 1D, a residual polynucleotide RP remains attached to the support material and a portion of the sample target polynucleotide G is hybridized to the residual polynucleotide RP. Depending upon the length of the base paired region between RP and the portion of the target polynucleotide strand attached to RP and the hybridization reaction conditions (salt, temperature, etc.), the portion of the target nucleotide strand attached to RP may or may not become subsequently detached. Such detachment is unlikely to significantly affect the conduct and sensitivity of the method of the present invention. A labeled cleavage fragment LCF, shown in FIG. 1D and containing all of the labeled probe polynucleotide LP no longer attached to the support (to the right) and likely including some portion of the distal (right) end of the half-restriction site R as diagrammed in FIGS. 1A-1C, and also including at least the detectable tag $T_1$, has now been separated from the residual polynucleotide RP. A second portion of the sample polynucleotide G is hybridized to the separated portion of the labeled probe polynucleotide LP. Accordingly, the labeled cleavage fragment LCF terminates at the restriction site, contains at least some transiently or stably double-stranded portion (the double-stranded portion being stable under certain conditions in a fashion similar to that discussed above for RP and some portion of the target polynucleotide sequence) and contains a detectable tag $T_1$.

According to this embodiment of the present invention, the labeled cleavage fragment LCF of FIG. 1D, once separated from the solid phase (which phase contains residual polynucleotide as shown in FIG. 1D as well as containing any reagent complexes still in their original form as depicted in FIG. 1A or in forms such as in FIG. 1B which have failed to form complete restriction endonuclease recognition sites in region R), is then detected. It is contemplated that, if the second polynucleotide SP contains its own detectable tag $T_2$, displayed second polynucleotide SP may be left in the vicinity of the solid phase during the restriction endonuclease-mediated cleavage step so that both labeled cleavage fragments LCF containing detectable tag $T_1$ and displaced second polynucleotide SP containing their detectable tag $T_2$ are separated simultaneously from the solid phase.

The separated liquid phase may then be analyzed for each tag separately or for the two tags simultaneously as would be preferred when the two tags must interact in order to produce a final signal. For example, if tags $T_1$ and $T_2$ are different enzymes, then substrates and cofactors for each enzyme may be added to the separated liquid phase, and disappearance of reactants or appearance of products of each enzymatic reaction may be determined after a suitable incubation period for the enzymatic reactions.

It is suficient for the present invention that the generation of labeled cleavage fragments LCF be detected by detecting tag $T_1$. Such fragments should be generated only when the target nucleotide sequence TNS of a sample polynucleotide G binds to the initial binding region IBR of the labeled probe polynucleotide LP and displaces the second polynucleotide SP far enough past the half-restriction site R to form a perfect restriction endonuclease recognition site R-R' such as that shown in FIG. 1C. Furthermore, labeled cleavage fragments LCF will only be generated if, after such (at least partial) nucleic acid strand displacement, a perfectly matched double-stranded nucleic acid segment is formed at half-restriction region R of the labeled polynucleotide LP such that the restriction endonuclease recognition site is adequately recognizable and cleavable by the appropriate restriction endonuclease enzyme specific for the formed recognition site. In those cases, however, in which a second detectable tag $T_2$ is present on the second polynucleotide SP, a second detectable event (displacement of the second polynucleotide SP from the labeled polynucleotide LP) may also be monitored. Such detectable displacement will occur if and only if a sample polynucleotide G contains sufficient homology with the target nucleotide sequence TNS of the labeled polynucleotide LP to bind (in the initial binding region IBR) and induce second polynucleotide strand displacement sufficiently through the double-stranded region of the initial reagent complex to force dissociation of the second polynucleotide SP from the labeled polynucleotide LP. It is believed that, depending upon reaction temperature, solution salt concentrations, and other reaction parameters, strand displacement of SP from the labeled polynucleotide LP need not proceed to the far right end of the double-stranded region as shown in FIGS. 1A and 1B, but merely that sufficiently few base pairs remain between the second polynucleotide SP and the labeled probe polynucleotide LP for subsequent spontaneous dissociation to occur. At moderate reaction temperatures (i.e., temperatures at or below about 50° C.), residual binding of as much as 10 base pairs between SP and the labeled polynucleotide LP may not greatly inhibit dissociation. At higher reaction temperatures (e.g., 50°-80° C.), residual binding between SP and the labeled polynucleotide LP of as much as about 20-30 base pairs may not greatly inhibit complete strand dissociation. A more complete discussion of this issue is contained within patent application U.S. Ser. No. 607,885; such discussion is incorporated herein by reference.

Since the monitoring of nucleic acid displacement and the monitoring of restriction enzyme cleavage of double-stranded nucleic acid structures depend on the detection of the signals from the related but distinct labels discussed in the previous two paragraphs, it is believed that (in certain cases) additional information can be drawn from the two events.

For example, one event may be used as a means of determining when the other event has been subject to interference by a sample polynucleotide sequence which: although effective to cause a second polynucleotide strand displacement, was not the precise target nucleotide sequence sought, and was ineffective to create a restriction endonuclease recognition site; or conversely, was effective to create a restriction endonuclease recognition site, but was ineffective to cause a second polynucleotide strand displacement. It is also contemplated that the detectable tags $T_1$ and $T_2$ may, rather than being separately monitored, be monitored for an interaction between themselves (e.g., as enzymes catalyzing successive reactions or as interacting chromophores), particularly in the liquid phase removed from the immobilized reagent complexes after exposure of reagent complexes to the sample being tested.

In the form of the present invention illustrated by the embodiment of FIGS. 1A-1D, the labeled probe polynucleotide is immobilized in the reagent complex prior to contact with the sample to be tested (which may or may not include sample polynucleotide). In some forms of the invention, the labeled probe polynucleotide LP contains a covalently bound immobilizable group (e.g., biotin or carbohydrate moieties) which is captured by an immobilized affinity agent (e.g., streptavidin or plant lectins, respectively,) bound to a solid matrix or support surface. In other forms, the homopolynucleotide segment of application Ser. No. 729,501 of P. D. Unger, et al., filed May 2, 1985, is provided in the labeled probe polynucleotide, to be captured by immobilized complementary homopolynucleotides (e.g., a poly-dC tail on the labeled probe polynucleotide which is captured by oligo-dG-cellulose resin). Either of the two forms of capturing could occur: after the sample is introduced to a solution containing the reagent complex of the present invention, and either before or after the restriction endonuclease cleavage reaction is carried out. In preferred forms of the invention, however, the labeled probe polynucleotide LP is either immobilized to or on a solid support when in the reagent complex (as illustrated in FIGS. 1A-1D), or is immobilized to or on a solid support after hybridization with any sample nucleic acids and before the restriction endonuclease cleavage reaction which is an integral portion of the method of the present invention. It is further contemplated that the reaction mixture (containing in many cases nucleic acid strands in forms similar to those shown in FIGS. 1A-1C) is washed to remove all extraneous sample materials which might interfere with the readout step of the present method before introduction of the restriction endonuclease.

The minimum length for the target binding region TBR of the labeled probe polynucleotide LP is generally determined as the sum of the minimum length of double-stranded region within the reagent complex and the minimum length of initial binding region IBR to promote efficient or stable nucleation of sample polynucleotide of labeled probe polynucleotide LP. The minimum length of the double-stranded region in the initial reagent complex is generally that sufficient to avoid non-specific dissociation of the second polynucleotide SP from the labeled probe polynucleotide LP under the chosen reaction conditions, particularly referring to conditions of temperature, salt concentrations and other chemical additives which may be present in the reaction solvent. Such double-stranded nucleic acid length is generally at least 15 base pairs, preferably at least 20 base pairs and more preferably between about 25 and about 200 base pairs. While excessively long double-stranded regions may not be necessarily disadvantageous, no particular advantage is seen in using double-stranded nucleic acid segments in the reagent complex that are longer than about 1000 base pairs. The initial binding region IBR of the labeled probe polynucleotide LP in the reagent complex is generally at least 10, preferably at least 50 and more preferably at least 100 nucleotides in length. It is not necessarily disadvantageous to use unusually long segments of the initial binding region IBR, however.

A necessary criterion for the present invention is that restriction sites recognizable by the restriction endonuclease used in the cleavage step of the present method are not created elsewhere within the duplex region of the product labeled probe polynucleotide-sample target polynucleotide hybrid molecule. Accordingly, it is preferred that the labeled probe polynucleotide contain no other sequences (e.g., hexanucleotide segments) identical to the half-restriction region R. It is further preferred that the second polynucleotide SP also not contain any sequences perfectly identical to the half-restriction site R either (1) because most restriction sites have a two-fold axis of symmetry and thus a corresponding sequence within the second restriction site R could cause the cleavable restriction site to form non-specifically with partially or wholly free (i.e., unhybridized) forms of the second polynucleotide SP, or (2) because the second polynucleotide SP itself could hybridize in any single-stranded portion with a single-stranded sample polynucleotide that is not a target polynucleotide and thereby non-specifically create a restriction site cleavable by an appropriate reagent restriction endonuclease, releasing the detectable tag $T_2$ (if present) into solution as part of a restriction endonuclease cleavage fragment and increasing the background signal level of the present method in a disadvantageous manner.

The lengths of the labeled probe polynucleotide LP and the second polynucleotide SP which do not participate in the nucleic acid base pairing shown in FIGS. 1A-1D are not particularly critical to the present invention. Accordingly, while there is no maximum to any of the unpaired lengths of the LP or SP nucleic acid strands, it is preferred to minimize such lengths except insofar as they provide spacing between the regions where base pairing occurs and either a detectable signal group or tag or any solid matrix or support or attachable moiety (e.g., biotin) to which the present reagent complex is attached. In general, therefore, spacings between the target binding region TBR of the labeled probe polynucleotide and any solid support (or an immobilizable moiety covalently attached to the labeled probe polynucleotide such as biotin) may be as short as 25 bases, but are preferably at least about 100 bases to enable any sample polynucleotide G to bind to the target binding region TBR as freely as possible. Spacing between the double-stranded region of the reagent complex shown in FIG. 1A and either detectable tag $T_1$ tag $T_2$ may be as short as a single nucleotide for tag $T_1$ or be no nucleotides for tag $T_2$ in the sense that tag $T_2$ may be attached to one of the nucleotides that are opposite to any of the nucleotides in the half-restriction site R of the labeled probe polynucleotide LP. However, the spacings between such double-stranded nucleic acid regions of the reagent complex and either tag $T_1$ or tag $T_2$ is preferably at least 10 nucleotides and are more preferably between about 25 and about 500 nucleotides in length. It should be evident from the copending applications referred to above that either of the detectable tags $T_1$ or $T_2$ may be multiple label moieties. Certain multiple labels and their method of attachment to nucleic acid strands are discussed fully in patent application U.S. Ser. No. 729,503, filed May 2, 1985; those discussions are incorporated herein by reference.

The reagent complex and method of the present invention may be used to determine any target nucleotide sequence of interest which contains at least one region of perfect nucleic acid base complementarity to a half-restriction site R. It is preferred, however, to adjust the target binding region TBR of any labeled probe polynucleotide LP to encompass one and only one particular half-restriction site R of the portion of any target polynucleotide to be bound by the TBR of the labeled probe. Half restriction sites recognizable by restriction endonucleases not used are of no adverse consequence.

Examples other than those discussed above in which two tags might be used for simultaneous or linked detection of certain nucleic acid hybridization events are those in which a family of related structural genes will have sequences sufficiently homologous to each other to displace the same second polynucleotide SP from the reagent complex of the present method, but only certain members of the family will have a base sequence exactly complementary to labeled probe polynucleotide LP in region R. Examples of such gene families (with some members of each of these families having sequences exactly complementary to the reagent complex half-restriction site R found within the labeled probe polynucleotide LP) include the globin, immunoglobulin and keratin genes or gene families contained within mammalian genomes.

The reagent complex of the present invention may be formed and prepared by any of the techniques described in any of the above-referenced patent applications. Thus, for example, a detectable tag $T_1$ may be attached to one end of a labeled probe polynucleotide LP by various chemical, biochemical, enzymatic or combined techniques, such as the combined chemical and enzymatic ligation techniques of E. Brown et al. described in patent application U.S. Ser. No. 729,700, filed May 2, 1985. The labeled probe polynucleotide LP so formed may then be hybridized to a second polynucleotide SP having an appropriate mismatched base or base segment. Thereafter, concurrently or earlier, the labeled probe polynucleotide LP may either be covalently attached at or near an end to a solid support or may have a moeity such as biotin covalently attached at or near an end which can be further bound to a solid support, not necessarily by covalent means; such attachment to a solid support can be before, during or after the subsequent assay steps.

Additionally, the techniques and nucleic acid constructs of patent application U.S. Ser. No. 729,504 of E. F Fritsch and Mary Collins, filed May 2, 1985, may be used in the preparation of reagent complexes to be used in the method of the present invention. In such techniques, the target binding region TBR (which is to be used in the labeled probe polynucleotide LP) and the base pairing segment of the second polynucleotide SP are each cloned into the same molecular cloning vector. The physical orientation of each cloned segment is such that, once the (vector plus insert or inserts) construct so formed is in single-stranded form (as the result, for example, of superinfection of a plasmid-containing bacterium such as *Escherichia coli* with a single-stranded bacterial virus such as M13 bacteriophage), the base pairing segment which is a precursor for the second polynucleotide SP will hybridize internally to a portion of one insert designated as containing a target binding region TBR. Since the two cloned nucleic acid insert segments are cloned separately into the same cloning vector, the base pair mismatch between some point in the half-restriction site R of the target binding region TBR found in the insert segment designated as the second polynucleotide SP may be designed and preserved through replication of the cloned vector-inserts construct (e.g., replicated as a plasmid, which contains cloned inserts as well as an M13 bacteriophage origin of replication). By chemical or enzymatic cleaving and attaching techniques analogous to those described in application U.S. Ser. No. 729,504, one may form an attachment between the labeled probe polynucleotide LP and any solid matrix or support material, as well as the attachment between LP and the first detectable tag $T_1$. If used, a second detectable tag $T_2$ may similarly be attached to the second polynucleotide SP. In preparing reagent complexes from such constructs for the present invention, if the various preparative cutting steps are based on restriction endonucleases, it is preferred in many forms of the present invention that a restriction endonuclease be used for preparative steps that is distinctly different from (i.e., is not an isochizomer of) the restriction endonuclease used in the post-strand displacement cleavage step of the present method. In particular, it is desirable that DNA segments not be present or created in the construct which will or can form perfectly base-paired restriction endonuclease recognition sites elsewhere in the reagent complex that are identical to the restriction site formable at the half-restriction site R within the TBR of the labeled polynucleotide LP as depicted in FIG. 1C. It is not intended, however, to exclude from preferred forms of the present invention the use of the restriction enzyme chosen for application during any preferred form of the method of the present invention so long as its use prior to the steps embodied within the present method (and especially the cleaving step (c)) does not prevent the production of a reagent complex with a unique half-restriction site R contained wholly within the TBR of the labeled probe polynucleotide as shown for illustrative purposes in FIGS. 1A-1D. It is preferred that any such use of the chosen restriction endonuclease prior to its use in the preferred forms of the method of the present invention (and especially the cleaving step (c)) be merely for purposes of eliminating improperly formed reagent complexes early in the process of reagent complex preparation, when such undesirable forms of reagent complexes have a perfectly base paired restriction endonuclease recognition site.

EXAMPLE

The following example illustrates a specific contemplated embodiment of the present method and demonstrates how the reagent complex of the present invention could be constructed and could be used. DNA from wild-type bacteriophage lambda (cf. *The Bacteriophage Lambda*, A.D. Hershey, ed. (Cold Spring Harbor, N.Y., 1971) is digested by the restriction endonuclease Pst I and a single-stranded fragment R, having its 3' end at nucleotide 16,236 (of the standard nucleotide map for lambda) and its 5' end at nucleotide 17,394 (of the standard map for lambda), is isolated by standard techniques. Fragment R is then cloned into the Pst I site of the M13 vector mp7. Both orientations of fragment R in the vector are obtained, and the orientation is chosen (clone $R_s$) that will result in production of the sense strand in the single-stranded progeny phage. The sense or coding DNA strand is as defined and used in F. Sanger, et al., Journal of Molecular Biology 162, 729-773 (1982). Digestion of purified single-stranded DNA from the progeny phage $R_s$ with restriction endonuclease Bam HI and purification of the lambda fragments results in a single-stranded DNA that can be attached at its 5' end to a hydrazide-containing latex bead by the procedures of Examples 9B and 11 of U.S. Ser. No. 729,700. A synthetic oligonucleotide (35-mer) which is labeled with phosphorus-32 (32-P) at its 5' end and which is completely complementary to nucleotides 16,267-16,301 near the 3' end of the long immobilized polynucleotide is hybridized thereto by standard techniques. This 32-P label is the signal moiety or tag for the probe polynucleotide.

A DNA restriction fragment obtained by a combined Xmn I - Hinc II restriction endonuclease digest of the 16,236-17,394 lambda DNA restriction fragment is isolated and cloned into the replicative form of M13 mp18 bacteriophage. This restriction digest yields a doubly blunt-ended DNA fragment from base 16,914 to base 17,076. The unique Kpn I endonuclease recognition sequence at map positions 17,053 to 17,058 is changed from GGTACC to CGATCA in the sense strand using the synthetic oligonucleotide:

5'-CATCCTCCCGATGAGCGCTGAT- 3' as a mutagenesis primer, employing standard M13 bacteriophage mutagenesis protocols (e.g., M. J. Zoller and M. Smith, *Methods in Enzymology*, vol. 100, R. Wu, et al., eds. (Academic Press, New York), pp. 468-500 (1983)). The correct mutant phage is identified and verified by DNA sequence analysis.

The appropriate single stranded bacteriophage carrying an insert completely complementary to an Xmn I - Hinc II sense strand, which sense strand has the sequence CGATGA at map positions 17,053-17,058, is then expanded and replicative form phage DNA is isolated. The phage DNA is digested with Bam H1 endonuclease and the single stranded fragment S containing DNA substantially complementary to the DNA strand R defined above is isolated by denaturing gel electrophoresis or an equivalent technique.

The DNA fragment S is hybridized to the latex-immobilized probe polynucleotide which already has the 32-P labeled 35-mer hybridized to it, yielding the desired reagent complex. Experimental hybridization conditions for formation of this reagent complex are as follows. About 0.05 pmol of probe polynucleotide immobilized on beads are combined with 2 pmol 32-P labeled 35-mer at 55° C. for 2 hours in 50 microliters of 1X HYB buffer (1 M NaCl, 50 mM Tris-HCl, pH 8). The beads are then washed by centrifuging at 11,000 g for 10 minutes, removing the supernatant and resuspending the pelleted beads in 1X HYB buffer. This centrifugation and resuspending procedure is repeated five times or until no further radioactivity is found in the supernatant. After resuspending the beads following the last wash step in 100 microliters of 1X HYB buffer, half of the beads (50 microliters) is used as "Probe A" (labeled probe polynucleotide) and the other half of the beads (50 microliters) is combined with 2 pmol of the mutated DNA segment S described above (i.e., the second polynucleotide). After incubation of this reagent mixture at 55° C. for 2 hours and repeated washing in 1X HYB buffer as above, the product reagent complex ("Probe B") is resuspended in 50 microliters of 1X HYB buffer.

Portions of the above labeled probe polynucleotide (Probe A) or reagent complex (Probe B) are challenged with test samples (a)–(c) where (a) negative control (distilled water);

(b) non-specific competitor DNA control (salmon sperm DNA denatured at 1 mg/mL in distilled water);

(c) competitor DNA [lambda single-stranded DNA or denatured double-stranded DNA completely complementary to the wild-type probe polynucleotide from at least the Xmn I site (map position 16,914) to the Pst I site (17,394); such DNA can be obtained by digestion of the 16,236–17,394 Pst I lambda DNA fragment with Xmn I alone and subsequent application of standard DNA fragment isolation and M13 cloning techniques] at 10 pmol/mL in distilled water.

Each reaction mixture contains 10 microliters of Probe A or Probe B, 2.5 microliters of 4X HYB buffer, 5 microliters of test sample DNA (a or b or c) and 2.5 microliters of distilled water. After incubating the reaction mixtures at 55° C. for one hour, each reaction mixture is cooled to room temperature. The reagent latex beads from each reaction mixture are then collected by centrifuging the mixtures at 11,000 g for 5 minutes, washed once in 50 microliters of 1X HYB buffer, and resuspended in 20 microliters of standard buffer for Kpn I restriction endonuclease digestion (e.g., 6 mM Tris-HCl, pH 7.5, 6 mM NaCl, 6 mM MgCl$_2$). Twenty units of Kpn I enzyme are then added to each reaction tube and the reaction mixtures incubated at 37° C. for two hours. The samples are then loaded into the wells of a 1% neutral agarose gel and electrophoresed. Autoradiograms of the resulting gel are then prepared using X-ray film and the films examined for results.

The results are expected to be as follows:

| Radioactivity Position | Reagent Probe: A | A | A | B | B | B |
|---|---|---|---|---|---|---|
| | Test sample DNA: a | b | c | a | b | c |
| Inlet Well: | All | Most | None or Weak | All | All | None or Weak |
| Position X (~800 nucleotides) | None | Weak | Most or All | None | None | Most or All |

In samples with no competitor DNA (test sample a), all of the radioactivity is expected to remain at the inlet well. In the sample with the unprotected labeled probe (Probe A) and non-specific competitor DNA (case Ab), a weak signal is expected at position X due to background events where salmon sperm DNA binds to the unprotected Kpn I half-restriction site in the probe polynucleotide and leads to non-specific endonucleolytic release of the labeled cleavage fragment. This weak signal is expected to be absent from case Bb, where the reagent complex of the present invention is used. In runs with the perfectly complementary competitor DNA (test sample c), most or all of the radioactivity is expected to be found at position X, indicative of a size of approximately 800 nucleotides.

Thus, as compared to the method of U.S. Ser. No. 652,218, the present invention should eliminate a source of background signal. Furthermore, if the second polynucleotide is labeled, a second type of signal, indicative of displacement, should be measurable in appropriate cases.

We claim:

1. A method for determining a target nucleotide sequence having a half-restriction site in the nucleic acid of a biological sample which comprises the steps:

(a) providing a reagent complex of:

(i) a labeled probe polynucleotide containing a target binding region which is substantially complementary to the target nucleotide sequence and which contains a unique half-restriction site completely complementary to the half-restriction site of the target nucleotide sequence; and (ii) a second polynucleotide hybridized to the labeled probe polynucleotide in at least a portion of the target binding region the portion including the unique half-restriction site of the target binding region;

the second polynucleotide containing at least one mismatched or unpaired nucleotide opposite to the unique half-restriction site of the labeled probe polynucleotide, whereby a restriction enzyme specific for the unique restriction site will not cleave the reagent complex;

(b) contacting the reagent complex with the sample under conditions in which the target nucleotide sequence, if present, will displace the second polynucleotide from the target binding region and form the unique restriction site in double-stranded form;

(c) specifically cleaving the labeled probe polynucleotide at the unique restriction site in double-stranded form to form a labeled cleavage fragment; and (d) detecting the labeled cleavage fragment.

2. The method of claim 1 wherein the labeled cleavage fragment is separated from uncleaved labeled probe polynucleotides after the specifically cleaving step (c) and prior to the detecting step (d).

3. The method of claim 2 wherein the labeled probe polynucleotide in the reagent complex is immobilized to a solid support.

4. The method of claim 3 wherein the labeled probe polynucleotide is immobilized adjacent to one of its ends and contains a detectable tag at or adjacent to the opposite end, and the unique half-restriction site is between the point of immobilization and the detectable tag.

5. The method of claim 4 wherein the second polynucleotide is hybridized to a portion of the target binding region.

6. The method of claim 5 wherein the second polynucleotide is hybridized to a portion adjacent to one end of the target binding region.

7. The method of claim 6 wherein the unique half-restriction site is intermediate within the portion of the target binding region hybridized to the second polynucleotide.

8. The method of claim 2 wherein the second polynucleotide is hybridized to a portion of the probe polynucleotide adjacent to one end of the target binding region.

9. The method of claim 8 wherein the unique restriction site is intermediate within the portion of the target binding region hybridized to the second polynucleotide.

10. The method of claim 1 wherein the second polynucleotide is hybridized to a portion adjacent to one end of the target binding region.

11. The method of claim 1 wherein the second polynucleotide contains a second detectable tag and the method further comprises the step:

(e) further detecting displaced second polynucleotide.

12. The method of claim 11 further comprising the step:

(f) comparing the quantity of detected labeled cleavage fragment from detecting step (d) with the quantity of detected displaced second polynucleotide from further detecting step (e).

13. A reagent complex for determining a target nucleotide sequence having a half-restriction site in the nucleic acid of a biological sample, comprising: (i) a labeled probe polynucleotide containing a target binding region which is substantially complementary to the target nucleotide sequence and which forms a unique half-restriction site complementary to the half-restriction site of the target nucleotide sequence; and (ii) a second polynucleotide hybridized to the labeled probe polynucleotide in at least a portion of the target binding region, the portion including the unique half-restriction site of the target binding region;

the second polynucleotide containing at least one mismatched nucleotide opposite to the unique half-restriction site of the labeled probe polynucleotide, whereby a restriction enzyme specific for the unique restriction site in double-stranded form will not cleave the reagent complex.

14. The reagent complex of claim 13 wherein the labeled probe polynucleotide is immobilized to a support.

15. The reagent complex of claim 14 wherein the labeled probe polynucleotide is immobilized adjacent to one end and contains a detectable tag adjacent to the opposite end, and the unique half-restriction site is between the point of immobilization and the detectable tag.

16. The reagent complex of claim 15 wherein the second polynucleotide is hybridized to a portion of the target binding region.

17. The reagent of claim 16 wherein the second polynucleotide is hybridized to a portion of the probe polynucleotide adjacent to one end of the target binding region.

18. The reagent complex of claim 17 wherein the unique half-restriction site is intermediate within the portion of the target binding region hybridized to the second polynucleotide.

19. The reagent complex of claim 14 wherein the second polynucleotide is hybridized to a portion of the labeled probe polynucleotide adjacent to one end of the target binding region.

20. The reagent complex of claim 13 wherein the second polynucleotide is hybridized to a portion adjacent to one end of the target binding region.

21. The reagent complex of claim 20 wherein the unique half-restriction site is intermediate within the portion of the target binding region hybridized to the second polynucleotide.

22. The reagent complex of claim 13 wherein the second polynucleotide contains a second detectable tag.

23. A diagnostic kit comprising the reagent complex of claim 22 and a restriction endonuclease capable of specifically cleaving the unique half-restriction enzyme recognition site when it is in a perfectly matched double-stranded form.

24. A diagnostic kit comprising the reagent complex of claim 14 and a restriction endonuclease capable of specifically cleaving the unique half-restriction enzyme recognition site when it is in a perfectly matched double-stranded form.

25. A diagnostic kit comprising the reagent complex of claim 13 and a restriction endonuclease capable of specifically cleaving the unique half-restriction enzyme recognition site when it is in a perfectly matched double-stranded form.

* * * * *